United States Patent [19]

Nunlist

[11] Patent Number: 4,595,487
[45] Date of Patent: Jun. 17, 1986

[54] SENSING PROBE HOLDER SYSTEM

[75] Inventor: Erwin J. Nunlist, Penfield, N.Y.

[73] Assignee: Kennecott Corporation, Cleveland, Ohio

[21] Appl. No.: 712,839

[22] Filed: Mar. 18, 1985

[51] Int. Cl.$^4$ .............................................. G01N 27/30
[52] U.S. Cl. .................... 204/433; 204/400; 204/286; 324/438
[58] Field of Search ............... 204/400, 404, 433, 435, 204/424, 425, 427, 428, 429, 279, 280, 286, 297 R; 324/438–439, 445, 446, 447, 448, 449, 450

[56] References Cited

U.S. PATENT DOCUMENTS

| | | | |
|---|---|---|---|
| 2,533,462 | 12/1950 | Ingram | 324/448 |
| 2,560,209 | 7/1951 | Borell et al. | 324/448 |
| 2,810,879 | 10/1957 | Cade et al. | 324/448 |
| 2,830,260 | 4/1958 | Chiocca | 324/446 |
| 2,830,261 | 4/1958 | Estelle | 324/446 |
| 2,878,354 | 3/1959 | Ellison | 204/404 X |
| 2,882,914 | 4/1959 | Wiley et al. | 324/448 X |
| 3,166,485 | 1/1965 | Lloyd | 204/400 X |
| 3,806,440 | 4/1974 | Gray et al. | 204/433 X |
| 3,868,022 | 7/1976 | Eng et al. | 204/286 X |
| 4,096,050 | 6/1978 | Kobayashi et al. | 204/428 |
| 4,203,807 | 5/1980 | Buchholz | 204/1 T |
| 4,285,791 | 8/1981 | Schmidt-Rabenau | 204/416 |
| 4,406,766 | 9/1983 | MacDonald | 204/433 |

FOREIGN PATENT DOCUMENTS 695911  8/1953  United Kingdom ............... 204/433

Primary Examiner—Howard S. Williams
Assistant Examiner—Nam X. Nguyen
Attorney, Agent, or Firm—R. Lawrence Sahr

[57] ABSTRACT

The present invention includes a system for mounting a sensor probe through the wall of a chemical vessel or other fluid container such that a sensing element can be located within. The system includes means for maintaining the sensing probe within the vessel in a fluid-tight, elevated temperature-resistant and corrosion-resistant seal. The system further includes provisions for removing, from the exterior of the reactor vessel, the sensing probe from the fixed sensing probe holder assembly which is within the interior of the reactor vessel. Further, means are included by which a sensing probe of an extended length which is mounted through the top of a chemical reactor vessel, can be inserted into and removed from the reaction vessel even with a low overhead situation above the uppermost portion of that reactor vessel.

9 Claims, 9 Drawing Figures

SENSING PROBE HOLDER SYSTEM

BACKGROUND OF THE INVENTION

1. Field of the Invention

The present invention relates generally to the field of sensing probes used in relation to chemical processing systems and more specifically, to systems for arranging and maintaining sensing probes in position to effectively perform their sensing functions in regard to chemical reactor vessels and containers used in the chemical processing field.

2. Background of the Prior Art

The processing of fluids, as is generally practiced in the chemical industry, usually requires the measurement of a variety of properties in chemical products during the various stages of their production. Such measurements are used to determine the precise nature of process conditions respectively at discreet points during the various phases through which materials pass, from the beginning of a chemical processing system to the end. The term chemical processing is used in the broadest sense to include the production of food products as well as the production of liquids and gases.

A significant portion of the field of chemical processing includes the use of enclosed reactor vessels of a variety of types, styles, and designs in which the discreet steps of the various processes to be performed, are accomplished. Within these reactor vessels, a variety of conditions are imposed on the chemicals passing therethrough which tend to cause or promote chemical, physical and/or electrical reactions which relate to steps in the processing of those chemicals. Many of the reactions which are caused or promoted within such reaction vessels tend to cause or promote corrosive reactions with the reactor vessels which contain them. Thus, sensing probes which are used in connection with such reactor vessels, or the flow lines associated with them, are required to be resistant to the corrosion. Needless to say, the vessels themselves, as well as their flow lines, also need to be resistant to such corrosion.

One highly successful approach to corrosion resistance in such reactor vessels, and within their associated flow lines, is to coat the surfaces within those vessels and flow lines, which are in contact with the corrosion produced by the chemical reactions, with glass. Another successful approach is to line the interiors of such reaction vessels and their associated flow lines with thin coatings of extreme corrosion resistant metals such as tantalum or titanium. Chemical reaction vessels of both types are produced by The Pfaudler Co. of Rochester, New York, and marketed respectively under the trademarks "Glasteel" and "Resista-Clad".

In addition to being corrosion resistant many chemical reactor vessels are required to operate for extended periods of time under conditions of pressure differentials of varying degrees, including both internal pressurization and vacuums. Also, such reactor vessels, in many cases, are required to operated at substantially elevated temperatures.

A variety of different sensing probes are readily available on the market. Many of these are adapted for corrosion resistant service and also for service where significant pressure and temperature differentials exist. For example, a glass coated pH sensing probe is disclosed in U.S. Pat. No. 3,787,307 and is presently marketed by The Pfaudler Co. of Rochester, N.Y., and the Pfaudler-Werke AG of Schwetzingen, Germany. A variety of other corrosion resistant sensors for sensing temperature, hydrogen ion concentration, corrosion resistant coating defects, localized pressures, etc. are likewise readily available in the marketplace. Usually these probes take the general physical shape of a long thin cylindrical body.

Many of the chemical reactor vessels that are used in the chemical processing industry tend to be rather large, exceeding several hundred gallons and upwards in size. Of these large vessels, many are stand-alone in that they are not attached to other items of machinery or equipment. Because of the nature of the processes to which such chemical reactor vessels are applied, in many cases the vessels need to be inside of a building. In respect to such buildings the chemical reactor vessels tend to be relatively large in relation to the building space alotted to them. Specifically, they tend to reach from the floor to the ceiling, being longer in length than in diameter size to save floor space. In addition, because of general requirements for gravity flow from the flow lines into the reactor vessels, in many cases there is an agglomoration of piping above the reactor vessels. The result of such arrangements is that there is little overhead room. That is, the distance between the uppermost part of the chemical reaction vessel in many situations tends to be very close to the roof or ceiling line of the interior of the building or very close to the overhead piping.

To be effective, the probes need to be rather long in length, extending through the uppermost portions of a chemical reactor vessel and extending through the interior of that same vessel to near its bottom or floor. The reason for this is that there is a need to sense various phenomena in the chemical fluids both when the vessel is full and when the vessel is nearly empty. The reason for inserting the probes through the top of the reactor vessel as well as other ports into the vessel which are subject to being opened from time to time, is to inhibit the occurance of spills and leaks of chemicals from the vessel itself.

Such sensing probes for use in relatively tall chemical reactors, because of the proximity of the roof line and/or pipe lines above the reactor vessel, are normally serviced and/or changed by shutting down the chemical process, evacuating the vessel and removing port covers from the vessel through which a man enters the vessel. This is a very difficult and time consuming procedure. In addition, it is quite dangerous to the individual who is required to perform the task. It is also an economically detrimental procedure because it requires that the chemical processing line, or at least that portion of it which uses that particular reactor vessel, must be shut down and taken out of service. Sensing probes need to be serviced and/or replaced, from time to time, to eliminate chemical product build-up on the sensor probe and to recalibrate the sensing elements to ensure accurate read-outs and monitoring capability, as well as correction of breakage and other service failures.

Thus there is a need for a system by which sensing probes can be detached from and withdrawn from the interior of reactor vessels without having to evacuate the vessel where liquids are being processed and without a man actually having to enter the vessel. Since most sensing probes are arranged vertically within reaction vessels, necessitating their introduction through the jacket of the vessel at or near the very uppermost portions of that vessel, there is a need for a system whereby a sensor probe can be introduced through an aperture in the top of the vessel such that it can be extended all the way to near the bottom or floor of the vessel in a low headroom situation.

SUMMARY OF THE INVENTION

The present invention includes a system for mounting a sensor probe vertically downward through the top of a reactor vessel such that a sensing element can be located adjacent to or near the bottom or floor section of that same reactor vessel. The system includes means for maintaining the sensing probe within the vessel in a fluid tight elevated temperature resistant and corrosion resistant seal. The system further includes provisions for removing from the exterior of the reactor vessel, the sensing probe from the fixed sensing probe holder assembly within the interior of the reactor vessel. Further, means are included by which a sensing probe of an extended length can be inserted into and removed from the reaction vessel even with a low overhead situation above the uppermost portion of reactor vessel. For a further understanding of the invention and for features and advantages thereof reference may be made to the following description and the drawings which illustrate prefered embodiments of the sensing probe holding system in accordance with the present invention.

DETAILED DESCRIPTION

Figure 1:
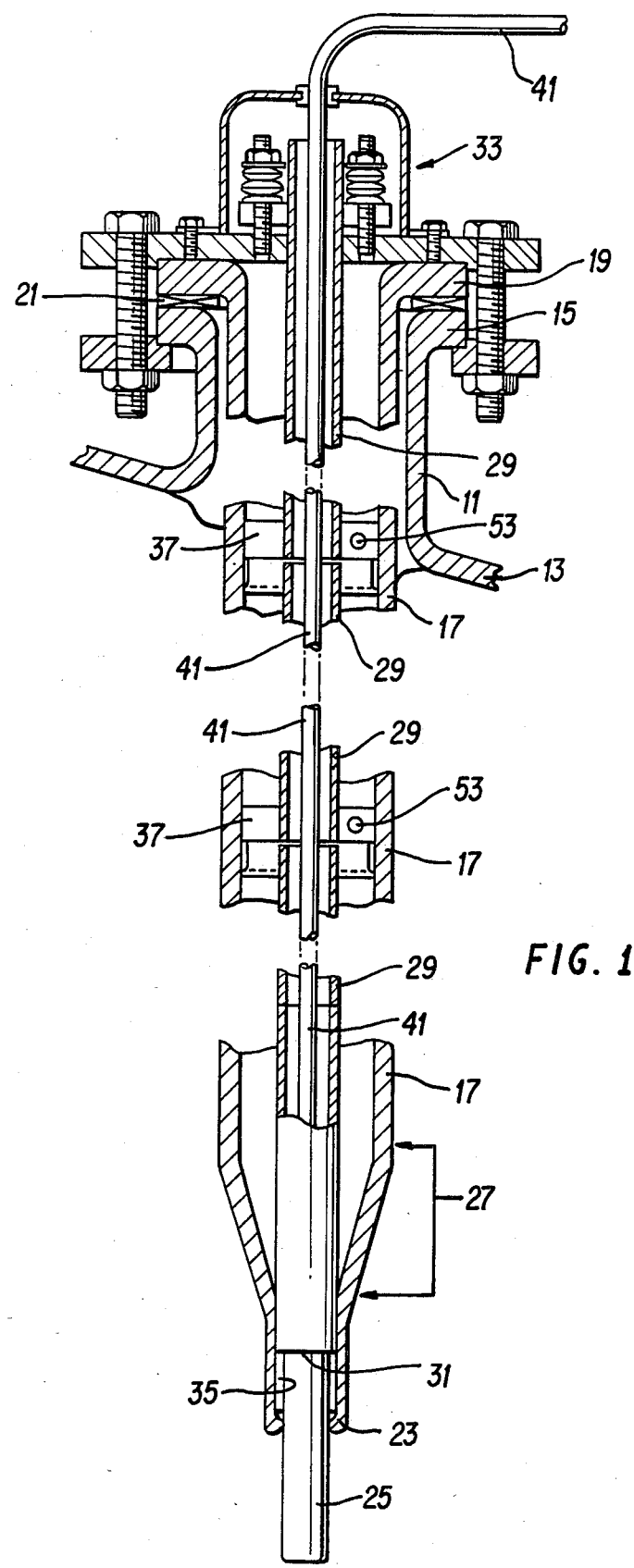
FIG. 1 illustrates an elevational cut-away view of one alternate prefered embodiments of the sensor probe mounting system as mounted to a top section of a chemical processing vessel.

Referring to FIG. 1 there is a flange mount 11 which extends from the top area 13 of a chemical reactor vessel. Horizontal flange 15 extends from the uppermost end of flange mount 11. Holder body 17, which includes holder flange 19, is mounted to horizontal flange 15 with gasket 21 interposed between the abutted faces there of, as will be further explained in reference to FIG. 8 hereinafter. Holder body 17 extends generally vertically, downwardly through horizontal flange 15 into the interior of the chemical reactor vessel. Although, only sections of holder body 17 are illustrated the length of holder body 17 is continuous and extends substantially to within a relatively short distance from the bottom or floor (not shown) of the chemical reactor vessel, with only sufficient distance between the seal end 23 of the holder body 17 and the bottom or floor of the chemical reactor vessel, to permit the sensor tip 25 to be mounted within the seal end 23 in a close but spaced-apart relationship from the floor or bottom of that chemical reactor vessel.

As will be noted in FIG. 1, holder body 17 has a tapered section 27. Tapered section 27, and its relationship to seal end 23 and sensor tip 25, is shown in an enlarged view in FIG. 3. Tapered section 27 is in the form of a frusto-conical section 27 and functions to form the transisition from the larger diameter of the extended length of holder body 17 to the smaller diameter of the upper end of seal end 23, as shown in FIG. 1.

As shown in FIG. 1, sensor tube 29 is concentrically mounted within the internal diameter of holder body 17. Sensor tube 29 extends throughout the length of holder body 17 including tapered section 27 to the stepped junction 31 that is made between sensor tube 29 and sensor tip 25 within seal end 23. At the oposite end of holder body 17, sensor tube 29 extends to about the upper end of holder flange 19 of holder body 17, as shown in FIG. 1. At the upper end of sensor tube 29, and mounted thereto is spring load assembly 33 which is shown in enlarged detail in FIG. 8. The function of spring load assembly 33 is to place a continuous linear axial thrust along the full length of sensor tube 29, urging it against packing seal 35 which is located within seal end 23 and which surrounds the upper portion of sensor tip 25. Since the linear thrust imposed by spring load assembly 33 extends for all the full length of sensor tube 29, sensor tube 29 in its entirety is spring loaded. That thrust load is maintained on packing seal 35 regardless of the degree of compaction thereof. In order to compress packing seal 35 adequately to insure a good seal, linear axial thrust force of about 500 pounds is recommended. It has been found that sensor tube 29, which is normally relatively thin does not do well, in terms of maintaining its rigidity and resistance to bend, when it is longer than about 40 inches. It is preferred that single piece sensor tubes 29 be no longer than about 30 inches.

A sensor tube 29 may be relatively long, far exceeding 30" or 40" in length. To insure the rigidity and resistance to bend moment, in such a case, axial aligning members 37 are placed along the length of that sensor tube 29 at intervals of about 30 inches. The axial aligning members 37 serve to maintain the sensor tube 29 in a position generally centered along the axis of the holder body 17, thus preventing bending or other distortion of the sensor tube when force is applied thereto by the spring load assembly 33.

As will be noted from FIG. 1, the sensor tube 29, when arranged in conjunction with the axial aligning members 37, is segmented within each axial aligning member 37. The elements of each of the axial aligning members 37, which will be described in detail hereinafter in reference to FIGS. 4, 5, 6 and 7, function as hinge members. When the full length of the sensor tube 29 is inserted into or withdrawn from the holder body 17, each sensor tube 29 segment, with its attached elements of the associated axial aligning member 37, may be pivoted to avoid obstructions in the immediate area of its withdrawal. Thus for example, low headroom above the reactor vessel caused by a low ceiling height or piping associated with that reactor vessel does not normally hinder the insertion or withdrawal of the sensor tube 29 from the reactor vessel. In the preferred length of each sensor tube 29 segment, no more than about 30 inches of that tube need be extended perpendicularly from the reactor vessel at any point in either the removal or insertion of the sensor tube 29 within the holder body 17.

Figure 2:
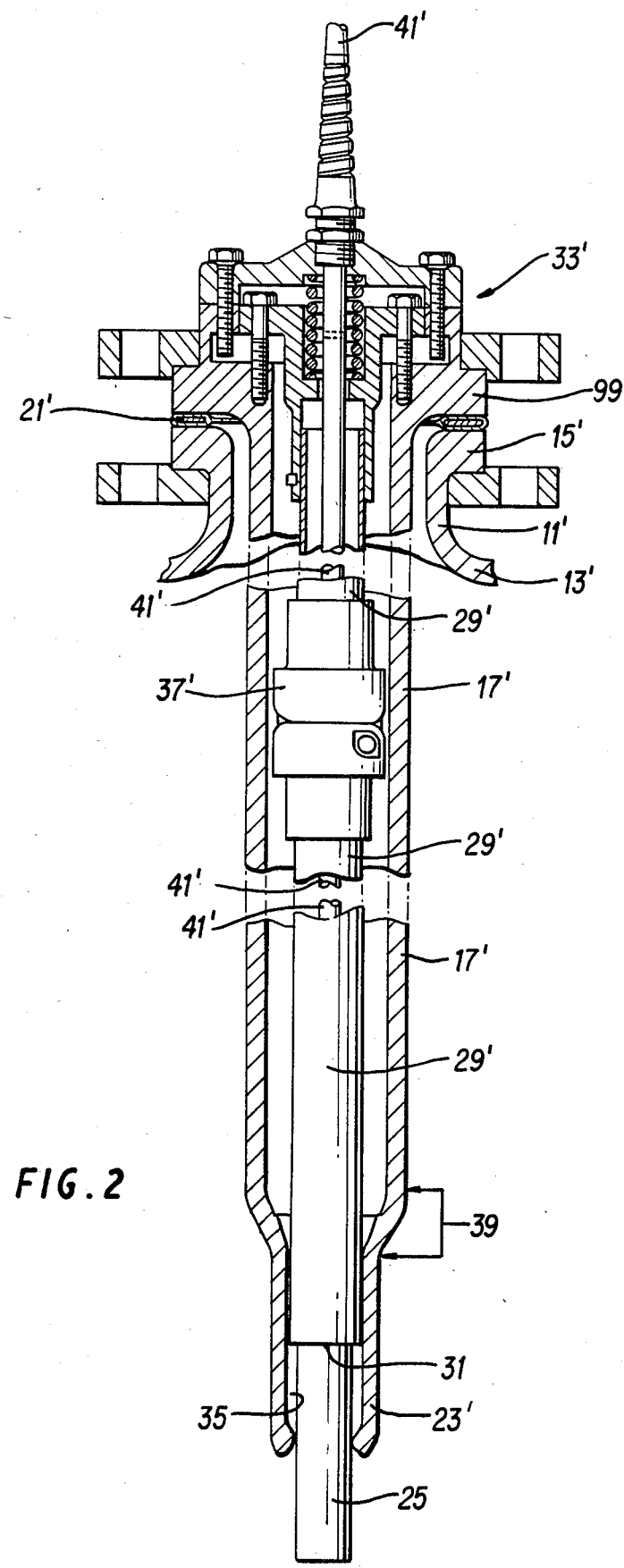
FIG. 2 illustrates a second alternate prefered embodiment in a elevational cut-away view of the sensor probe mounting system as mounted to the upper portion of a chemical processing vessel.

Referring to FIG. 2, there is shown a second alternate preferred embodiment of the sensing probe holder system. Generally, all of the elements described for the first alternate preferred embodiment, as shown in FIG. 1, are the same for the second alternate preferred embodiment as shown in FIG. 2. Each of those elements is identified by the same number as the elements identified in reference to FIG. 1 with the exception that all are primed. The main significant difference between the embodiment shown in FIG. 1 and the embodiment shown in FIG. 2 is found in the specific details of the spring load assemblies 33 and 33'. Spring load assembly 33' will be described in detail hereinafter in reference to FIG. 9.

The only other difference between the embodiment shown in FIG. 1 and the embodiment shown in FIG. 2 is that the embodiment shown in FIG. 2 does not contain a tapered section 25 but is replaced with bell section 39. Bell section 39 serves an identical function to that served by taper section 27 described above in relation to the embodiment shown in FIG. 1. In the embodiments shown in FIGS. 1 and 2, a flexible conduits, 41 and 41' connect the sensor tips 25 and 25' respectively, to sensor operating and monitoring systems (not shown).

Figure 3:
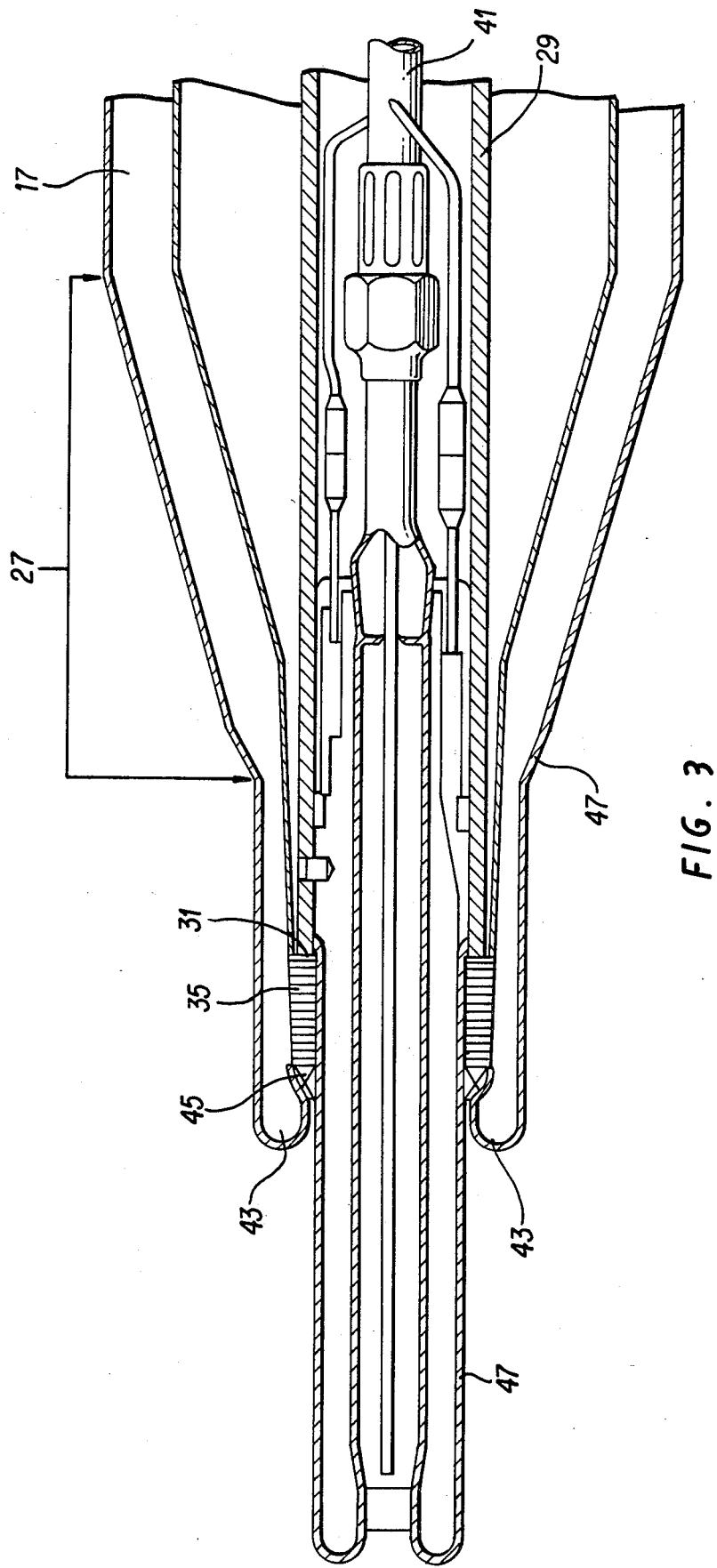
FIG. 3 shows an enlarged elevational cut-away view of the lower portion of the sensor probe mounting system as viewed in FIGS. 1 and 2.

Referring to FIG. 3, there is shown an enlarged view of the lower portion of the sensing probe holder system shown in FIG. 1. This cut-away view specifically shows the interior arrangement of the flexible conduit 41 and the connections from it to a pH sensing device which comprises an example of the sensor tip 25. The specific details of the internal arrangement of the pH sensing device will not be described further because they are not specifically part of the present invention.

Packing seal 35 may be formed from any appropriate packing material which is capable of withstanding the corrosion, temperature differentials and pressure differentials to which it will be exposed within the chemical reactor vessel. A preferred material for packing seal 35 is a flexible graphite material manufactured by Union Carbide Corporation, Danbury, Conn. and marketed under the trademark "Grafoil". This material is more fully described in U.S. Pat. Nos. 3,404,061 and 4,068,853.

Of particular note in relation to FIG. 3 is the tapered bore forming most of the interior of seal end 23. The tapered bore extends from the lower junction of tapered section 27 to retainer step 43 of seal end 23. Retainer step 43 includes a smaller inside diameter than that of the lower end of seal end 23 and functions as a seat for a seal retaining ring 45. Seal retainer ring 45 functions to prevent packing seal 35 from leaking or oozing out of the lower end of seal end 23 when packing seal 35 is under compression from the spring loaded force applied to it by sensor tube 29. Seal retainer ring 45 is shaped to conform to the transition between the smaller inside diameter of retainer step 43 and the relatively larger inside diameter of seal end 23. Seal retainer ring 45 can be formed from any appropriate material which is capable for withstanding the corrosion, temperature differentials, and pressure differentials to which the sensor probe is to be subjected. A preferred material is a fiber filled PTFE fluorocarbon composition marketed under the trademark "Teflon" by E. I. DuPont de Nemours & Co. It is necessary that the seal retainer ring 45 be sufficiently resistant to compression to withstand deformation caused by the linear axial thrust force placed on packing seal 35 by sensor tube 29.

The inside bore of seal end 23 is slightly tapered being about 1/16 inch larger in diameter at the end thereof which is adjacent to taper section 27 than the end diameter which is adjacent to retainer step 43. Thus, when packing seal 35 is compressed by the linear axial thrust force applied by sensor tube 29, it will form and take the shape of the smaller diameter of seal end 23 in which it is seated. When sensor tube 29 is withdrawn from holder body 17, packing seal 35 it will readily release from the tapered inside diameter of seal end 23 but will adhere to the adjacent section of sensor tip 25 and step junction 31 and, thus, be withdrawn with the sensor probe. On reinsertion of the sensor probe, either the already-formed packing can be replaced, or, if necessary, new packing can be wrapped around sensor tip 25 adjacent to step junction 31. If new packing is used to form a new packing seal 35, when the sensor probe is inserted back within holder body 17 and compressed by the linear axial thrust force applied by sensor tube 29, that new packing will be formed into the above described shape of packing Seal 35, upon compression.

The overall exterior of holder body 17 is subjected to the ambient conditions within the reactor vessel. Thus, it should have, at least, the same resitance to corrosion, temperature differentials, and pressure deffierentials as the balance of the interior of the reactor vessel. For example, if the reactor vessel is internally coated with glass, the exterior of the holder body 17 should, likewise, be coated with glass. FIG. 3 shows glass coating 47 which is adhered to the underlying base metal of the holder body 17. Glass coating 47 also extends around the lower end of seal end 23 and preferably coats the internal tapered bore of seal end 23. Likewise, sensor tip 25 may also be glass coated as is shown in FIG. 3.

Figure 4:
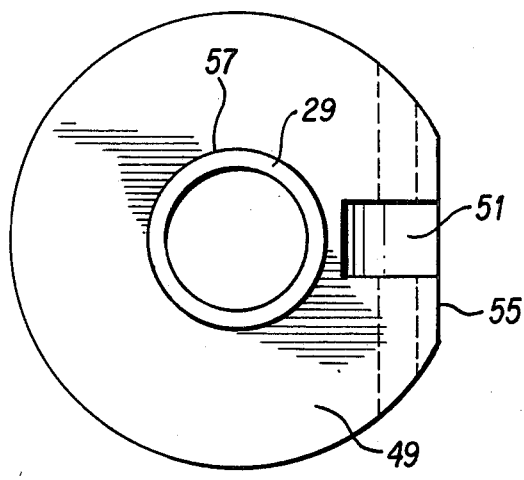
FIG. 4 is a bottom plan view of the upper section of the sensor tube drive and centering system as shown in FIGS. 1 and 2.

FIGS. 4-7 show various views of the major elements of axial aligning member 37 as mentioned above. FIG. 4 shows female aligning ring 49, generally in the shape of a cylindrical section, with an end section of a segment of sensor tube 29 fixed thereto. Hinge insert section 51 is formed to extend radially inwardly from the periphery of the female aligning ring 49. Hinge insert section 51 is cross drilled to fit hinge pin 53 about which the elements of axial aligning member 37 pivot. The outside diameter of female aligning ring 49 is sized to slip fit within the interior of holder body 17. Flat 55 is formed across the peripheral face of female aligning ring 49 to permit clearance for ease of pivotation of the elements of axial aligning member 37 which occurs at the point of entrance or egress thereof from holder flange 19, as the sensor probe is being either inserted or withdrawn from holder body 17. The plane of flat face 55 is arranged to be both parallel to hinge pin 53 and parallel to the central axis of the segment of sensor tube 29 to which female aligning ring 49 is fixed.

Figure 5:
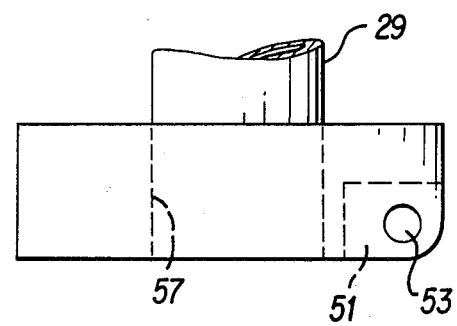
FIG. 5 is an elevation view of the upper section shown FIG. 4.

FIG. 5 shows an elevational view of female aligning ring 49 as fixed to the end of a segment of sensor tube 29. Sensor tube 29 extends through the bore 57 of female aligning ring 49 to the point where the end of the segment of sensor tube 29 is even and flush with that face of female aligning ring 49 which abuts the adjacent face of male aligning ring 59.

Figure 6:
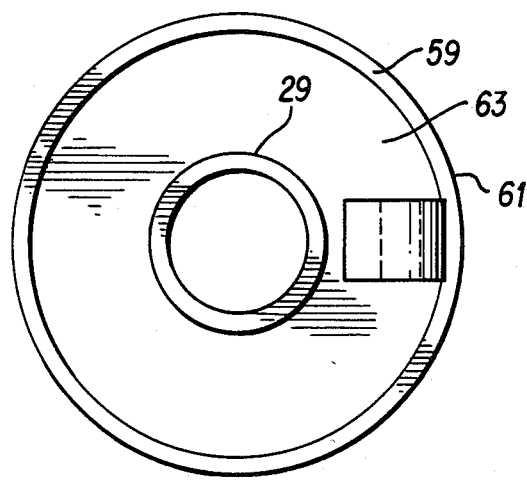
FIG. 6 is a top plan view of the lower section of the sensor tube drive and centering system as shown in FIGS. 1 and 2.

Male aligning ring 59 is shown in plan view in FIG. 6. The faces of female aligning ring 49 and male aligning ring 59 which abut are shown in FIG. 4 and FIG. 6, respectively. Male aligning ring 59 includes stepped section 61 which is sized to match the outside diameter of female aligning ring 49. The main body 63 of male aligning ring 59 is shown slightly smaller in diameter. Stepped section 61 permits ease of entry of axial aligning member 37 at holder flange 19 when inserting the sensor probe into the holder body 17 due to less contact between the touching surfaces thereof with the interior of holder body 17.

Figure 7:
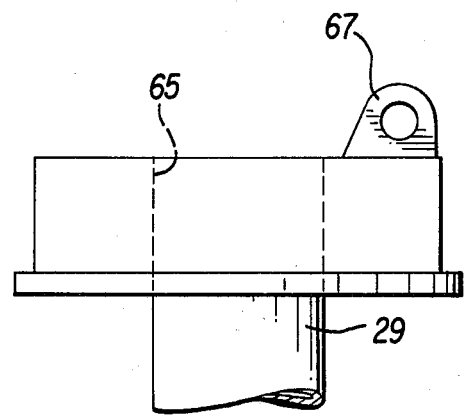
FIG. 7 is an elevational view of the lower section shown in FIG. 6.

Male aligning ring 59 is also fixed to the end of a segment of sensor tube 29 with the end of that segment of sensor tube 29 extending through the bore 65 of male aligning ring 59 as shown in FIG. 7. That end of the segment of sensor tube 29 is also even and flush with the face of male ring aligning 59 which abuts the adjacent face of female aligning ring 49. Male aligning ring 59 has a hinge extension 67 which is sized and positioned to fit within hinge insert section 51 of female aligning ring 49. Hinge extension 67 is cross bored to a size slightly larger than the diameter of hinge pin 53, such that the cross bore of hinge extension 67 will permit male aligning ring 59 to freely pivot about the diameter of hinge pin 53.

In lengthy sensor probes where axial aligning members 37 are used and sensor tube 29 is segmented, the abutting faces of female aligning rings 49 and male aligning rings 59 serve to transmit the axial thrust force applied to the sensor tube 29, by spring load assembly 33 from each segment of sensor tube 29 to the next successive segment of sensor tube 29. The above described sizing and arrangement of the elements of axial aligning member 37 permit the linear movement of the sensor probe on its insertion or extraction from holder body 17, and are preferred because of the relatively close fit between the outside diameters of female aligning ring 49 and stepped section 61 of male aligning ring 59 with the interior of holder body 17, as will be readily understood by those with skill in the field.

On pivotation of male aligning ring 59 about hinge pin 53, in relation to female aligning ring 49, flexible conduit 41 will flex with that pivotation and slide within sensor tube 29 to provide sufficient extension of length of that flexible conduit 41 to compensate for the separation of the two adjacent segment ends of sensor tube 29.

Preferably, the upper ends of sensor tubes 29 and 29' are threaded externally to accept the elements of spring load assemblies 33 and 33', respectively. However, alternative means of mounting spring load assemblies 33 and 33' to the upper ends of sensor tubes 29 and 29', respectively, may be used.

Figure 8:
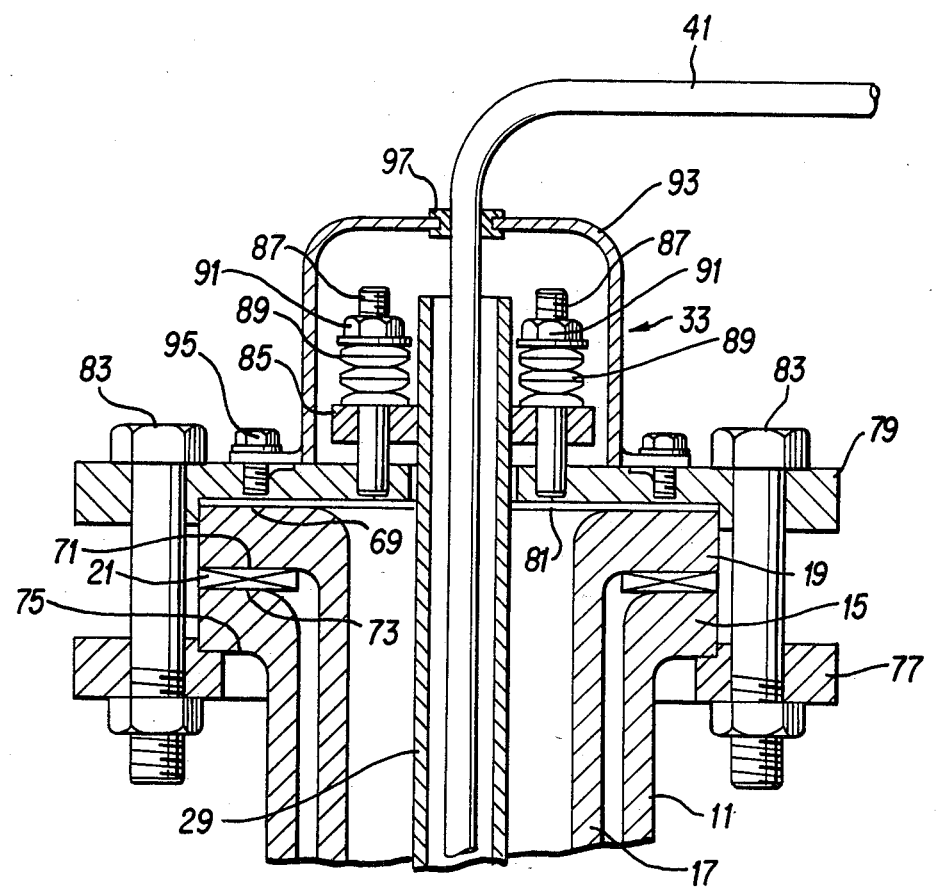
FIG. 8 is an enlarged cut-away elevational view of the upper portion of the sensor probe mounting system as shown in FIG. 1.

Referring to FIG. 8, as mentioned before, there is shown an enlarged sectional elevational view of the upper end of the sensor probe holder system which includes spring load assembly 33. Holder flange 15 is flared outwardly from holder body 17 such that upper face 69 and lower face 71 are formed. Upper face 69 and lower face 71 are both in the form of flat planes which are parallel to each other and perpendicular to the central axis of holder body 17. Flange mount 11, likewise, includes an upper face 73 and a lower face 75, both of which form planes which are parallel to each other and perpendicular to the central axis of holder body 17. The peripheral diameters of flange mount 11 and horizontal flange 15 are generally equivalent. Interposed between lower face 71 and upper face 73 is gasket 21, which is sealably compressed between those two faces, as will be well understood by those with skill in the field.

Flange compression ring 77 is fitted below lower face 75 of flange mount 11. Flange compression ring 77 can either be of one-piece construction or of "split-flange" construction, both of which are well known to those with skill in the field. Flange compression ring 77 includes an internal bore and a plurality of bolt holes concentrically surrounding that internal bore in conventional fashion as is well known to those with skill in the field. Platform plate 79 is predrilled and tapped appropriately as will be explained hereinafter. One function of platform plate 79 is cooperation with flange compression ring 77. Thus, a plurality of concentrically arranged bolt holes are drilled through platform plate 79 to match the bolt holes, previously mentioned, which have been drilled into flange compression ring 77.

Platform plate 79 is positioned to abut with upper face 69 of holder flange 19 with gasket 81 interposed there between. The major plane of platform plate 79 is positioned parallel to the plane of upper face 69 and the major plane of flange compression ring 77 is positioned parallel to the plane of lower face 75. Compression bolt fasteners 83 which comprise nut and bolt combinations are mounted through the matching bolt holes of flange compression ring 77 and platform plate 79, respectively, and tightened equally to a degree sufficient to form a leak free joint by way of the compression of gasket 21.

Platform plate 79 includes a center bore which is sized slightly larger in diameter than the diameter of sensor tube 29, thus, permitting a sliding fit of sensor tube 29 through that central bore of platform plate 79 as is shown in FIG. 8.

Thrust flange 85 is in the form of a flat round plate disk. It includes a central bore which is threaded to match the threaded upper end of sensor tube 29. Also, thrust flange 85 includes a plurality of stud holes arranged equidistantly and concentrically around the threaded central bore thereof. Each of these stud holes is sized to provide a slip fit over spring studs 87. Spring studs 87 are arranged concentrically and equidistantly spaced apart surrounding the central bore of platform plate 79. Spring studs 87 are threaded into drilled and tapped holes in platform plate 79. Spring studs 87 are positioned to extend perpendicularly upward from the major plane of platform plate 79.

In assembly, thrust flange 85 is threaded onto the previously described upper threaded end of sensor tube 29. Then thrust flange 85 is fitted over and downwardly onto platform plate 79, with spring studs 87 extending upwardly through the stud holes of thrust flange 85. Above thrust flange 85 are mounted a plurality of disk spring washers 89. These disk spring washers 89 are fitted onto the portins of spring studs 87 which extend through thrust flange 85. The number of disk spring washers 89 being equivalent for each of the spring studs 87. Above the disk spring washers 89, onto each of spring studs 87, is threaded a tension nut 91. Each of these tension nuts 91 is threadably tightened against the disk spring washers beneath to flatten those washers out, thus creating a thrust force linearly downwardly along the axis of sensor tube 29 to ultimately compress the packing seal 35 beneath the remote end of the sensor tube 29, as explained above.

Surrounding the upper end of sensor tube 29 is seal cover 93. Seal cover 93 also encloses and seals thrust flange 85, spring studs 87 with disk spring washers 89 and tension nuts 91 mounted thereto. Seal cover 93 is appropriately shaped and sized to enclose all the foregoing as shown in FIG. 8.

Seal cover 93 is bolted to platform plate 79 by use of cover bolts 95 threadably engaged in drill and tapped holes in platform plate 79 as illustrated in FIG. 8. Flexible conduit 41, which extends from the upper end of sensor tube 29, also extends through seal 97 which is centrally located in the uppermost part of seal cover 93, directly above the central axis of sensor tube 29. Seal 97 and seal cover 93 prevent the ingress and egress of foreign materials and/or trace materials which have escaped from the chemical reactor vessel.

Figure 9:
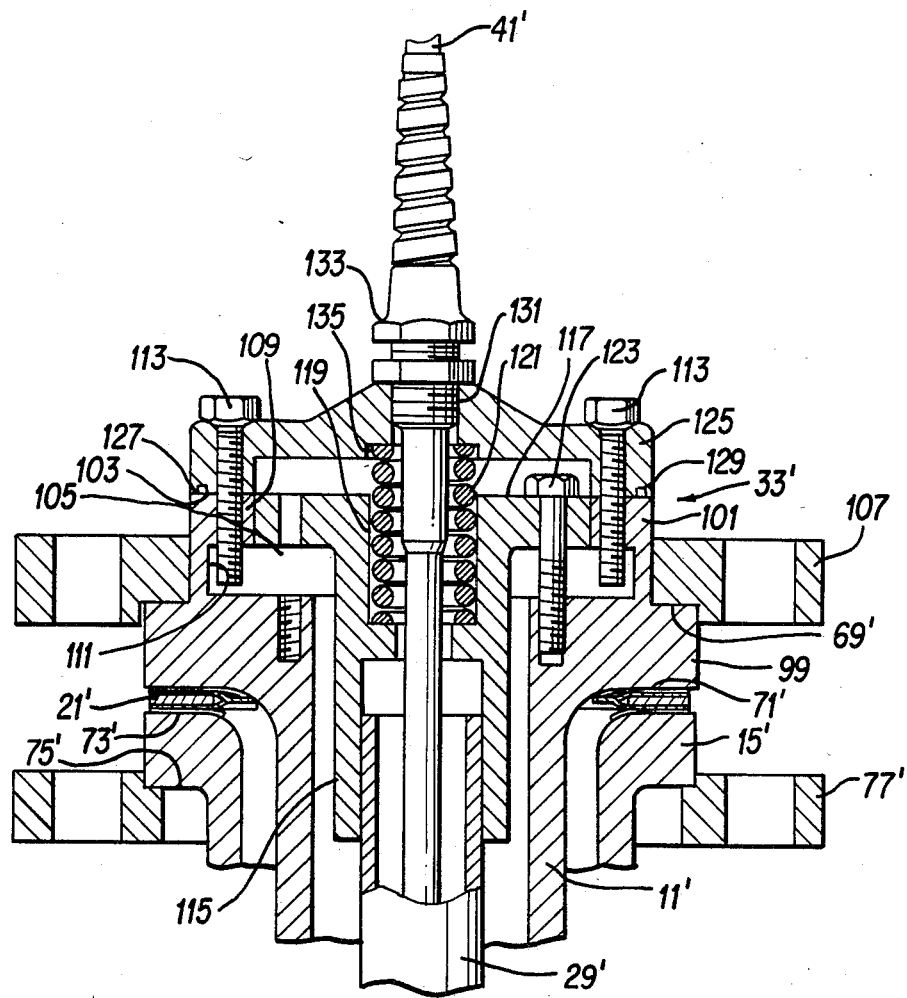
FIG. 9 in an enlarged cut-away elevational view of the upper section of the sensor probe mounting system shown in FIG. 2.

Referring to FIG. 9, there is shown an enlarged elevational sectional view the upper end of the sensor probe holding system which is illustrated in FIG. 2. The elements illustrated in FIG. 9, which are generally equivalent in design and function to those illustrated in FIG. 8, are numbered the same as those same elements identified in relation to FIG. 8, with the exception that where the numbers are the same in relation to FIG. 9, they are primed. Specifically, in FIG. 9 there is illustrated flange mount 11', horizontal flange 15', holder flange 19', gasket 21', sensor tube 29', flexible conduit 41', upper face 69', lower face 71' upper face 73', lower face 75' and flange compression ring 77'. Spring load assembly 33', illustrated in FIG. 9 is different from spring load assembly 33 illustrated in FIG. 8.

Referring to FIG. 9, holder flange mounting bracket 99 is substituted for holder flange 19 as shown in FIG. 8. Holder flange mounting bracket 99 is similar to holder flange 19 with the exception that there is a mounting platform extension 101 which extends upwardly from the upper face 69' thereof. Mounting platform extension 101 includes mounting face 103, which is a plane positioned perpendicular to the central axis of sensor tube 29'. Mounting face 103 includes an axial concentric circular vertically recessed cavity 105 concentrically surrounded by a plurality of equidistantly spaced-apart threaded bolt holes. Upper face 69 of holder flange mounting bracket 99 also include a plurality of equidistantly spaced-apart threaded bolt holes, concentrically arranged. The diameter of the bolt circle of the threaded bolt holes in upper face 69 is less than the diameter of circular cavity 105.

In the arrangement of the spring load assembly 33 illustrated in FIG. 9, a second flange compression ring 107, identical in shape, size and bolt hole arrangement to flange compression ring 77', is also used. Second flange compression ring 107 is arranged in relation to upper face 69 of holder flange mounting bracket 99 in identical fashion to the way that flange compression ring 77' is arranged in relation to lower face 75' of horizontal flange 15' as illustrated in FIG. 9. Compression fasteners 83, although not shown in FIG. 9, are applied to flange compression ring 77 and second flange compression ring 107 in the same manner that compression fasteners 83 are applied to flange compression ring 77 and platform plate 79 as illustrated in FIG. 8. Thus, a fluid tight seal is effected by the relationship of seal 21' to lower face 71' and upper face 73'.

Referring again to mounting platform extension 101 of holder flange mounting bracket 99, the circular cavity 105 thereof includes a smooth bore beneath which is an undercut section of a larger diameter than that of the bolt hole circle diameter, described above, in relation to mounting face 103 and as shown in FIG. 9. The bolt holes of mounting face 103 extend into the open space created by undercut section 111, thus providing relief for the extension cap bolts 113 which extend therein.

Spring holder 115 is generally shaped in the form of a cylindrical section, topped by an enlarged diameter spring holder flange 117. The lower end or body of spring holder 115 is bored and threaded to mate with the threaded end of sensor tube 29' and on assembly spring holder 115 is threaded onto sensor tube 29'. A smaller diameter bore extends axial through the full length of spring holder 115 and is sized to permit flexible conduit 41' to slip therethrough.

A concentric recess 119 is formed to extend vertically downwardly from the top end of spring holder 115 and sized to fit the outside diameter of coil spring 121. The threaded bore of spring holder 115 does not extend upwardly far enough to meet the lowest depth of recess 119, the two merely being connected by the central bore provided for flexible conduit 41'. Spring holder flange 117 is externally smooth about its perphery, and sized to slip fit within bore 109 of circular cavity 105. In assembly spring holder flange 117 is inserted into bore 109.

Bolt holes extend from the top of spring holder 115 vertically, downwardly to match the bolt holes in upper face 69' as illustrated in FIG. 9. Lock bolts 123 are inserted therethrough to rigidly and stationarily fix spring holder 115 in relation to holder flange mounting bracket 99. By loosening or tightening lock bolts 123, spring holder 115 can be adjusted upwardly or downwardly within bore 109.

Seal cap 125 includes mating face 127 which, on assembly, mates with mounting face 103. Bolt holes are arranged vertically through seal cap 125 to match the threaded bolt holes in mounting face 103. And cap bolts 113 extend through seal cap 125 to hold seal cap 125 in a sealed relationship to mounting face 103. That seal is provided by O-ring 129 which is fitted into in an O-ring groove formed in mating face 127.

Seal cap 125 includes port 131 into which flexible conduit seal 133 is threadably inserted. Flexible conduit 41' extends through flexible conduit seal 133 and downwardly into sensor tube 29'. Port 131, at the bottom thereof, includes counterbore 135 which is of a diameter sufficient to permit the upward end of coil spring 121 to fit therein. Counterbore 135 serves to locate coil spring 121 in relation to recess 119 and to contain coil spring 121 in concentric relation to flexible conduit 41'. On assembly of seal cap 125 to holder flange mounting bracket 99, coil spring 121 is compressed, thus providing an axial thrust load onto spring holder 115 which, in turn, imparts linear axial thrust to sensor tube 29'. That thrust is ultimately transmitted at the lower end of sensor tube 29' to packing seal 35 to compress it.

According to the provisions of the patent statutes, what is consider to represent the best embodiments of the present invention and their alternative preferred constructions and their respective best modes of operation have been illustrated and described. However, it is to be understood that within the scope of the appended claim the invention may be practiced otherwise than as specifically illustrated and describe.

What is claimed is:

1. A sensing probe holder system, operable from the exterior of a closed fluid container, to insert and withdraw a sensor probe assembly, respectively, into and out of said closed fluid container comprising:
(a) a sensor probe assembly comprising:

(i) a sensor tube, segmented into a plurality of segments, and further comprising hinge means, connecting each of said segments together in linear succession, said hinge means which also permit the pivotation of each of said segments from the next of said segments in linear succession at any point where said segments or any of them are withdrawn from holder means;

(ii) a sensor tip mounted to one end of said sensor tube; and (iii) conduit means, connected to said sensor tip and extending through said sensor tube, adapted to connect said sensor tip to apparatus which is capable of interacting with said sensor tip, said apparatus being located remote from said closed fluid container;

said sensor probe assembly further comprising a cylindrical section;

(b) holder means adapted to surround and enclose said sensor probe assembly except for a portion of said sensor tip;

(c) compressible seal means adapted to seal a junction between said holder means and said portion of said sensor tip which is not surrounded and enclosed by said holder means;

(d) means for said sensor tube to apply compression force to said seal means;

(e) means for applying and continuously urging linear axial thrust to said sensor tube which results in compression force being applied to said seal means;

(f) means for mounting said holder means sealably through a wall of said closed fluid container and positioning said sensor tip in substantial contact with fluid which is within said closed fluid container;

(g) means for removably mounting said sensor probe assembly within said holder means, said means for removably mounting which are entirely operable from the exterior of said closed fluid container; and (h) means for causing said compressible seal means to be concurrently removed with the removal of said sensor probe assembly."

2. The invention of claim 1 wherein said holder means is a holder body in the general form of a hollow tube and into which said sensor probe assembly is fitted.

3. The invention of claim 1 wherein said seal means is a packing seal, and further comprising packing seal retainer means which prevents said packing seal from being compressed out of a junction between said holder means and said portion of said sensor tip which is not surrounded and enclosed by said holder means.

4. The invention of claim 1 wherein said sensor tip is adapted to measure the pH of said fluid within said closed fluid container.

5. The invention of claim 1 wherein said closed fluid container is a chemical reactor vessel.

6. The invention of claim 1 wherein said hinge means are further adapted to substantially center, and maintain substantially centered, said sensor probe assembly within said holder means.

7. The invention of claim 1 wherein said means for applying and continuously urging linear axial thrust comprises compression spring means engaged with the end portion of said sensor tube which is remote from said end of said sensor tube to which said sensor tip is mounted.

8. The invention of claim 1 wherein said means for said sensor tube to apply compression force to said seal means comprises a stepped junction between said sensor tube and said sensor tip, the step of said stepped junction being larger in diameter than said sensor tip, said step being in a linear contact relationship with said compressible seal means.

9. The invention of claim 1 wherein said means for mounting said holder means coprises:

(a) holder flange means mounted to the end of said holder means and positioned adjacent to said wall of said closed fluid container;

(b) wall flange means, surrounding an aperture through said wall, and mounted to said wall, adapted to sealably mate with said holder flange means;

(c) gasket means interposed between said holder flange means and said wall flange means; and (d) compression means adapted to apply force to said holder flange means resulting in the compression of gasket means and a fluid tight seal between said holder flange means and said wall flange and said gasket means therebetween.

* * * * *